US010227890B2

United States Patent
Prociw et al.

(10) Patent No.: US 10,227,890 B2
(45) Date of Patent: Mar. 12, 2019

(54) RESONANT MODES IN SPRAYS

(71) Applicant: Delavan Inc, West Des Moines, IA (US)

(72) Inventors: Lev A. Prociw, Johnston, IA (US); Jason A. Ryon, Carlisle, IA (US)

(73) Assignee: Delavan, Inc., West Des Moines, IA (US)

( * ) Notice: Subject to any disclaimer, the term of this patent is extended or adjusted under 35 U.S.C. 154(b) by 123 days.

(21) Appl. No.: 15/240,484

(22) Filed: Aug. 18, 2016

(65) Prior Publication Data

US 2018/0051586 A1  Feb. 22, 2018

(51) Int. Cl.
| | |
|---|---|
| F01D 21/00 | (2006.01) |
| G01H 13/00 | (2006.01) |
| G01N 29/48 | (2006.01) |
| G01N 29/032 | (2006.01) |
| B05B 12/00 | (2018.01) |

(Continued)

(52) U.S. Cl.
CPC .......... *F01D 21/003* (2013.01); *B05B 12/004* (2013.01); *F02C 7/22* (2013.01); *G01H 3/04* (2013.01); *G01H 9/00* (2013.01); *G01H 13/00* (2013.01); *G01N 29/032* (2013.01); *G01N 29/48* (2013.01); *F05D 2220/32* (2013.01); *F05D 2240/24* (2013.01); *F05D 2240/35* (2013.01); *F05D 2260/83* (2013.01); *G01H 11/06* (2013.01)

(58) Field of Classification Search
CPC .......... F01D 21/003; G01H 3/04; G01H 9/00; G01H 13/00; G01H 11/06; G01N 20/032; G01N 29/14; G01N 29/222; G01N 29/4427; G01N 29/46; G01N 29/48
See application file for complete search history.

(56) References Cited

U.S. PATENT DOCUMENTS

| | | | | |
|---|---|---|---|---|
| 4,165,635 A | * | 8/1979 | Komaroff | B60F 3/0053 73/114.45 |
| 4,905,897 A | * | 3/1990 | Rogers | A01M 7/0096 239/1 |

(Continued)

FOREIGN PATENT DOCUMENTS

| | | | |
|---|---|---|---|
| JP | 02-247058 | * | 10/1990 |
| JP | H02247058 A | | 10/1990 |
| RU | 2004119615 A | | 12/2005 |

OTHER PUBLICATIONS

Extended European Search Report dated Dec. 22, 2017, issued during the prosecution of European Patent Application No. EP 17186766.6 (7 pages).

*Primary Examiner* — Helen C Kwok

(74) *Attorney, Agent, or Firm* — Locke Lord LLP; Scott D. Wofsy; Joshua L. Jones

(57) ABSTRACT

A system for inspecting spray nozzles includes a nozzle operatively connected to a source of pressurized liquid for issuing a spray from the nozzle. The system also includes a sensor positioned to detect frequencies of resonant modes in the spray. The nozzle and sensor can each be mounted to a spray test booth. A method of inspecting a spray nozzle includes issuing a liquid from a spray nozzle as a spray and using a sensor to detect frequencies of resonant modes in the spray. The sensor can include a diaphragm and detecting frequencies can include impinging at least some of the spray on the diaphragm, and monitoring vibrations of the diaphragm.

13 Claims, 2 Drawing Sheets

(51) Int. Cl.
*F02C 7/22* (2006.01)
*G01H 9/00* (2006.01)
*G01H 3/04* (2006.01)
*G01H 11/06* (2006.01)

(56) References Cited

U.S. PATENT DOCUMENTS

| | | | | |
|---|---|---|---|---|
| 5,315,306 A | * | 5/1994 | Doughty | B05B 12/082 |
| | | | | 342/104 |
| 5,349,811 A | * | 9/1994 | Stickler | F02C 9/28 |
| | | | | 60/39.281 |
| 5,753,806 A | * | 5/1998 | Ryan, III | F02D 41/28 |
| | | | | 239/74 |
| 6,171,366 B1 | * | 1/2001 | Vicard | B01D 46/0075 |
| | | | | 55/283 |
| 7,250,087 B1 | * | 7/2007 | Tyson | A47L 15/0049 |
| | | | | 134/18 |
| 7,856,963 B2 | | 12/2010 | Hopley et al. | |
| 8,154,711 B1 | * | 4/2012 | Scheer | B05B 12/082 |
| | | | | 356/3.01 |
| 2002/0190203 A1 | * | 12/2002 | Valaskovic | H01J 49/165 |
| | | | | 250/288 |
| 2004/0144175 A1 | * | 7/2004 | Sinha | G01N 13/02 |
| | | | | 73/579 |
| 2005/0263611 A1 | * | 12/2005 | Gotoh | B05B 11/3042 |
| | | | | 239/102.1 |
| 2006/0225489 A1 | * | 10/2006 | Giles | G01N 29/032 |
| | | | | 73/64.53 |
| 2007/0152081 A1 | * | 7/2007 | Chou | B05B 17/0646 |
| | | | | 239/102.2 |
| 2010/0170329 A1 | * | 7/2010 | Greeves | F02M 65/001 |
| | | | | 73/114.45 |
| 2011/0239621 A1 | | 10/2011 | Meneely et al. | |
| 2013/0296812 A1 | * | 11/2013 | Bangera | A61M 35/00 |
| | | | | 604/290 |
| 2014/0200837 A1 | | 7/2014 | Blair et al. | |
| 2016/0177709 A1 | * | 6/2016 | Li | E21B 47/101 |
| | | | | 166/249 |
| 2016/0245253 A1 | * | 8/2016 | Maragliulo | F02M 65/001 |
| 2018/0052088 A1 | * | 2/2018 | Sarkar | G01N 15/0227 |

\* cited by examiner

RESONANT MODES IN SPRAYS

BACKGROUND OF THE INVENTION

1. Field of the Invention

The present disclosure relates to spray technologies, and more particularly to injectors and nozzles such as used in fuel injection for gas turbine engines and the like.

2. Description of Related Art

Injectors and nozzles for fuel injection in gas turbine engines are high-performance, precision manufactured components. They are required to operate predictably and with a high degree of reliability. As such rigorous quality control tests are performed on injectors and nozzles before placing them in service. The tests are designed to verify the individual nozzle or injector is properly manufactured and will perform as designed. Nozzles or injectors failing the quality control tests are scrapped or reworked.

Such conventional methods and systems have generally been considered satisfactory for their intended purpose. However, there is still a need in the art for improved nozzles, injectors, and testing techniques and apparatus therefor. The present disclosure provides a solution for this need.

SUMMARY OF THE INVENTION

A method of inspecting a spray nozzle includes issuing a liquid from a spray nozzle as a spray and using a sensor to detect frequencies of resonant modes in the spray. The sensor can include a diaphragm and detecting frequencies can include impinging at least some of the spray on the diaphragm, and monitoring vibrations of the diaphragm.

The sensor can include a vibration transducer connected to the diaphragm, wherein detecting frequencies includes generating a signal using the vibration transducer. The method can include analyzing the signal from the vibration transducer to detect resonances in the spray. It is also contemplated that the sensor can include a laser vibrometer optically connected to the diaphragm, wherein detecting frequencies includes generating a signal using the laser vibrometer. The method can include analyzing the signal from the laser vibrometer to detect resonances in the spray.

Using a sensor can include impinging a single discrete jet on the diaphragm. It is also contemplated that the diaphragm can be cylindrical, and using a sensor can include impinging a spray cone or multiple discrete jets on an inside surface of the cylindrical diaphragm.

A system for inspecting spray nozzles includes a nozzle operatively connected to a source of pressurized liquid for issuing a spray from the nozzle. The system also includes a sensor positioned to detect frequencies of resonant modes in the spray. The nozzle and sensor can each be mounted to a spray test booth.

The sensor can include a diaphragm. The sensor can include a vibration transducer connected to the diaphragm for generating a signal indicative of spray incident on the diaphragm. A spectrum analyzer can be operatively connected to receive the signal from the vibration transducer to detect resonances in the spray. It is also contemplated that the sensor can include a laser vibrometer optically connected to the diaphragm for generating a signal indicative of spray incident on the diaphragm. A spectrum analyzer can be operatively connected to receive the signal from the laser vibrometer to detect resonances in the spray.

The diaphragm can be positioned for impingement of a single discrete jet from the nozzle on the diaphragm. The sensor can include a drum with the diaphragm stretched across one end thereof. The diaphragm can include a steel foil material. It is also contemplated that the diaphragm can be cylindrical and can be positioned for impingement of a spray cone or multiple discrete jets from the nozzle on an inside surface of the cylindrical diaphragm.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
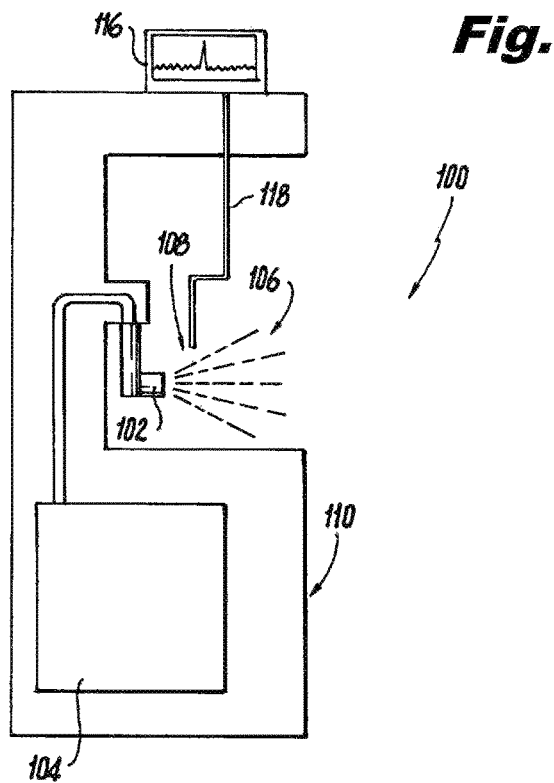
FIG. 1 is a schematic view of an exemplary embodiment of a system constructed in accordance with the present disclosure, showing a nozzle operatively connected to a spray test booth with a sensor for detecting resonant frequencies in the spray from the nozzle.

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 100. Other embodiments of systems in accordance with the disclosure, or aspects thereof, are provided in FIGS. 2-4, as will be described. The systems and methods described herein can be used to detect unwanted resonant frequencies in the spray issued from nozzles such as in fuel injectors for gas turbine engines.

It has been found in conjunction with the information disclosed herein that fuel nozzles can emit audible tones during spray measurements. The tones can be indicative of flow resonances which can be symptomatic of deviations from design specifications. Fuel flow from some injector designs may contain resonant modes, or regular pulses, due to flow phenomena associated with the nozzle or because the nozzle amplifies upstream oscillations. This may vary from injector to injector in a production run, and depending on the resonant frequencies present, the presence of resonant frequencies can potentially contribute to detrimental combustion waves in a combustor section of a gas turbine engine which can be damaging to combustor and turbine geometries. Detecting the presence of resonant modes in the spray after the injector, as opposed to detecting resonant modes inside the injector or in a flame downstream of an injector, can be used as a quality control measure thanks to the systems and methods disclosed herein. Flow oscillations in a nozzle may arise due to unsuspected flow conditions occurring within the flow components (such as vortex whistle) or may be a response to a resonant mode in one of the internal components.

System 100 for inspecting spray nozzles includes a nozzle 102 operatively connected to a source 104 of pressurized liquid for issuing a spray 106 from the nozzle 102. Spray 106 can be a spray of droplets, one or more discrete jets, or any other suitable type of spray. The system also includes a sensor 108 positioned to detect frequencies of resonant modes in the spray 106. The nozzle 102 and sensor 108 are each mounted to a spray test booth 110.

Figure 2:
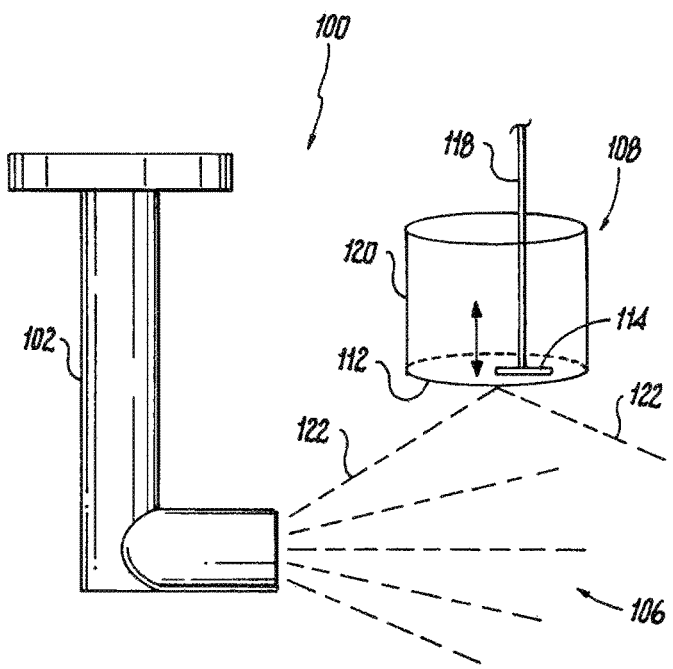
FIG. 2 is a schematic view of an exemplary embodiment of the sensor of FIG. 1, showing a sensor drum with a diaphragm and transducer.

Referring now to FIG. 2, the sensor 108 includes a diaphragm 112 with a vibration transducer 114 connected to the diaphragm 112 for generating a signal indicative of spray 106 incident on the diaphragm 112. A spectrum analyzer 116, shown in FIG. 1, is operatively connected to receive the signal, e.g. wirelessly or by way of lead 118, from the vibration transducer 114, e.g., a thin film piezoelectric transducer, to detect resonances in the spray 106. The sensor 108 includes a drum 120 with the diaphragm 112 stretched across one end thereof. The diaphragm 112 can include a steel foil material, or any other suitable material. The diaphragm 112 is positioned for impingement of a single discrete jet 122 from the nozzle 102 on the diaphragm 112, however those skilled in the art will readily appreciate that sensor 108 can be positioned so that any suitable number of discrete jets impinge on the diaphragm 112. Multiple sensors 108 can be used to monitor multiple discrete jets. The double arrows in FIG. 2 indicate vibration of diaphragm 112.

Figure 3:
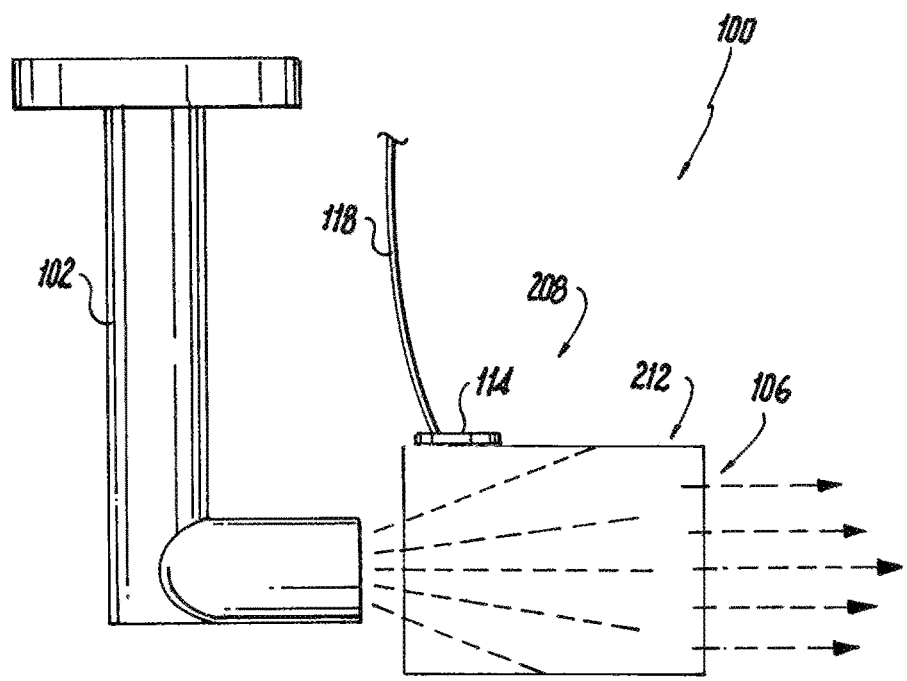
FIG. 3 is a schematic view of another exemplary embodiment of the sensor of FIG. 1, showing a cylindrical diaphragm positioned to have the spray cone of the nozzle impinge thereon.

With reference now to FIG. 3, another exemplary embodiment of a sensor 208 is shown that can be used to sense vibration in a spray cone issued from nozzle 102 to identify pulsation in the spray pressure field. The diaphragm 212 of sensor 208 is cylindrical and is positioned for impingement of a spray cone or multiple discrete jets from the nozzle 102 on an inside surface of the cylindrical diaphragm 212. In other words, spray 106 impinges about the full circumference of diaphragm 212. Transducer 114 is mounted to diaphragm 212 for generating signals indicative of vibrations from the spray 106 incident on diaphragm 212.

Figure 4:
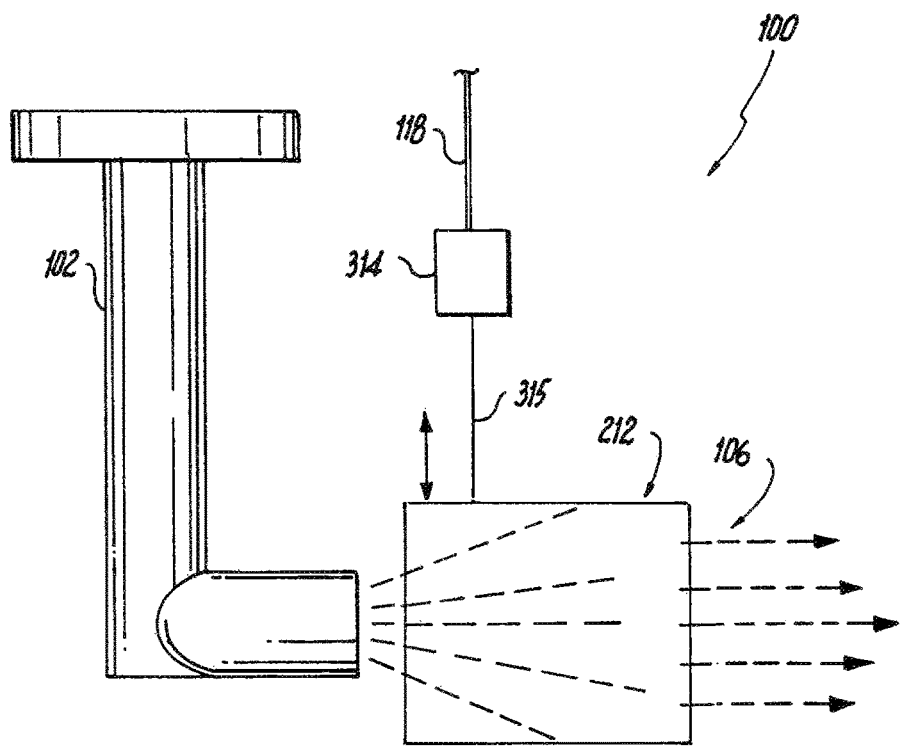
FIG. 4 is a schematic view of another exemplary embodiment of the sensor of FIG. 3, showing a laser vibrometer optically coupled to the cylindrical diaphragm to monitor vibration thereof.

With reference now to FIG. 4, another exemplary embodiment of a sensor 308 is shown, which includes a cylindrical diaphragm 212 positioned like that described above with reference to FIG. 3. The sensor 308 includes a laser vibrometer 314 optically connected to the diaphragm 212 for generating a signal indicative of spray 106 incident on the diaphragm 212. Laser vibrometer 314 shines a laser beam 315 on diaphragm 212 and monitors changes of the resulting laser reflection indicative of vibration in diaphragm 212 to generate a signal for spectrum analyzer 116, which can be connected wirelessly or by lead 118 to detect resonances in the spray 106. While shown in conjunction with a cylindrical diaphragm 212, those skilled in the art will readily appreciate that a laser vibrometer can be used in addition to or in lieu of a vibration transducer 114 with a cylindrical diaphragm 212 or diaphragm 112 as shown in FIG. 2. The double arrows in FIG. 4 indicate vibration of diaphragm 112.

A method of inspecting a spray nozzle includes issuing a liquid from a spray nozzle, e.g., nozzle 102, as a spray, e.g., spray 106, and using a sensor, e.g., sensors 108, 208, or 308, to detect frequencies of resonant modes in the spray. The sensor can include a diaphragm, e.g., diaphragm 112 or 212, and detecting frequencies can include impinging at least some of the spray on the diaphragm, and monitoring vibrations of the diaphragm.

The sensor can include a vibration transducer, e.g., transducer 114, connected to the diaphragm, wherein detecting frequencies includes generating a signal using the vibration transducer. The method can include analyzing the signal from the vibration transducer to detect resonances in the spray, e.g., using a spectrum analyzer 116. Spectrum analyzer 116 can perform a fast Fourier Transform (FFT), or any other suitable domain transformation, on the raw data or time averaged raw data, to determine resonant frequencies, e.g. resonant peaks, present in the signal from the sensors described herein. It is also contemplated that the sensor can include a laser vibrometer, e.g., laser vibrometer 314, optically connected to the diaphragm, wherein detecting frequencies includes generating a signal using the laser vibrometer. The method can include analyzing the signal from the laser vibrometer to detect resonances in the spray.

Using a sensor can include impinging a single discrete jet on the diaphragm. It is also contemplated that the diaphragm can be cylindrical, and using a sensor can include impinging a spray cone or multiple discrete jets on an inside surface of the cylindrical diaphragm.

The methods and systems of the present disclosure, as described above and shown in the drawings, provide for spray testing nozzles with superior properties including detecting resonant frequencies in sprays issued from nozzles. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method of inspecting a spray nozzle comprising:
    issuing a liquid from a spray nozzle as a spray; and
    detecting frequencies of resonant modes in the spray with a sensor, further comprising monitoring vibrations of a diaphragm of the sensor, the vibrations being due to the spray impinging upon the diaphragm, wherein the diaphragm is cylindrical, and wherein using a sensor includes impinging a spray cone or multiple discrete jets on an inside surface of the cylindrical diaphragm.

2. The method as recited in claim 1, further comprising exciting a vibration transducer in operative communication with the diaphragm.

3. The method as recited in claim 2, further comprising analyzing a signal from the vibration transducer and detecting resonances in the spray.

4. The method as recited in claim 1, further comprising detecting frequencies with a laser vibrometer in optical communication with the diaphragm.

5. The method as recited in claim 4, further comprising analyzing the signal from the laser vibrometer to detect resonances in the spray.

6. The method as recited in claim 1, further comprising impinging a single discrete jet on the diaphragm.

7. A nozzle spray sensing arrangement comprising:
    a sensor positioned and configured to sense pulses in a spray of fluid exiting from a nozzle, wherein the sensor includes a diaphragm, wherein the diaphragm is cylindrical and is positioned for impingement of a spray cone or multiple discrete jets from the nozzle on an inside surface of the cylindrical diaphragm.

8. The system as recited in claim 7, wherein the nozzle and sensor are each mounted to a spray test booth.

9. The system as recited in claim 7, wherein the sensor includes a vibration transducer connected to the diaphragm for generating a signal indicative of spray incident on the diaphragm.

10. The system as recited in claim 9, further comprising a spectrum analyzer operatively connected to receive the signal from the vibration transducer to detect resonances in the spray.

11. The system as recited in claim 7, wherein the sensor includes a laser vibrometer optically connected to the diaphragm for generating a signal indicative of spray incident on the diaphragm.

12. The system as recited in claim 11, further comprising a spectrum analyzer operatively connected to receive the signal from the laser vibrometer to detect resonances in the spray.

13. The system as recited in claim 7, wherein the diaphragm is positioned for impingement of a single discrete jet from the nozzle on the diaphragm.

* * * * *